United States Patent [19]

Fey et al.

[11] Patent Number: 5,492,923
[45] Date of Patent: Feb. 20, 1996

[54] SUBSTITUTED PYRIDINES AND 2-OXO-1,2-DIHYDROPYRIDINES

[75] Inventors: Peter Fey, Wuppertal; Jürgen Dressel, Radevormwald; Rudolf Hanko, Essen; Walter Hübsch, Wuppertal; Thomas Krämer, Wuppertal; Ulrich Müller, Wuppertal; Matthias Müller-Gliemann, Solingen; Martin Beuck, Erkrath; Hilmar Bischoff, Wuppertal; Stefan Wohlfeil, Hilden; Dirk Denzer; Stanislav Kazda, both of Wuppertal; Johannes-Peter Stasch, Solingen; Andreas Knorr, Erkrath; Siegfried Zaiss, Wuppertal, all of Germany

[73] Assignee: Bayer Aktiengesellschaft, Leverkusen, Germany

[21] Appl. No.: 235,831

[22] Filed: Apr. 29, 1994

[30] Foreign Application Priority Data

May 6, 1993 [DE] Germany ............ 43 14 963.4

[51] Int. Cl.$^6$ .................... C07D 401/10; A61K 31/44
[52] U.S. Cl. .................................. 514/340; 546/276
[58] Field of Search ...................... 514/340; 546/276

[56] References Cited

FOREIGN PATENT DOCUMENTS

| 0419048 | 3/1991 | European Pat. Off. . |
|---|---|---|
| 0445811 | 9/1991 | European Pat. Off. . |
| 0487745 | 6/1992 | European Pat. Off. . |
| 0500297 | 8/1992 | European Pat. Off. . |
| 2696745 | 4/1994 | France . |
| 113681 | 5/1992 | Japan . |

OTHER PUBLICATIONS

Chemical Abstract vol. 114 (1991) 247 301 x.

Chemical Abstract vol. 115 (1991) 114531x.

Chemical Abstract vol. 115 (1991) 159 173 v.

Russell Ross, The Journal of Cell Biology, vol. 50, 1971, pp. 172–186.

Wade Organic Chemistry p. 349. Prentice–Hall Inc. 1987.

Clark et al. Principles of Psychopharmacology. Academic Press. New York. 1970. p. 167.

*Primary Examiner*—Jane Fan
*Attorney, Agent, or Firm*—Sprung Horn Kramer & Woods

[57] ABSTRACT

Substituted pyridines and 2-oxo-1,2-dihydropyridines are prepared by reaction of correspondingly substituted halogenobenzenes with tetrazolylboronic acids. The substituted pyridines and 2-oxo-1,2-dihydropyridines according to the invention can be employed as active compounds in medicaments, in particular for the treatment of arterial hypertension and atherosclerosis.

10 Claims, No Drawings

SUBSTITUTED PYRIDINES AND 2-OXO-1,2-DIHYDROPYRIDINES

The invention relates to substituted pyridines and 2-oxo-1,2-dihydropyridines, processes for their preparation and their use in medicaments, in particular as antihypertensive and anti-atherosclerotic agents.

It is known that renin, a proteolytic enzyme, splits off the decapeptide angiotensin I from angiotensinogen in vivo, angiotensin I in turn being broken down to the hypertensive octapeptide angiotensin II in the lung, the kidneys or other tissues. The various effects of angiotensin II, such as, for example, vasoconstriction, Na$^+$ retention in the kidney, release of aldosterone in the adrenal gland and an increase in the tonicity of the sympathetic nervous system, act synergistically in the sense of increasing blood pressure.

Angiotensin II moreover has the property of promoting the growth and multiplication of cells such as, for example, cardiac muscle cells and smooth muscle cells, these growing to an increased extent and proliferating with various disease states (for example hypertension, atherosclerosis and cardiac insufficiency).

In addition to inhibition of renin activity, a possible use for intervention in the renin-angiotensin system (RAS) is inhibition of the activity of angiotensin converting enzyme (ACE) and blockade of angiotensin II receptors.

Biphenyl-substituted pyrimidones moreover are known from the publications EP 407 342, 424 317, 435 827 and 419 048.

The present invention relates to substituted pyridines and 2-oxo-1,2-dihydropyridines of the general formula (I)

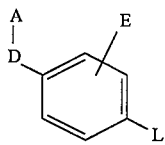

(I)

in which

A represents a radical of the formula

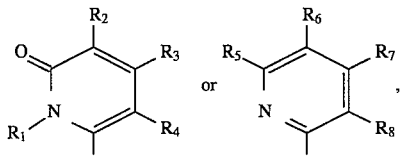

wherein $R^1$ denotes straight-chain or branched alkyl having up to 10 carbon atoms, which is optionally substituted by cycloalkyl having 3 to 6 carbon atoms, hydroxyl or by straight-chain or branched alkoxy or alkylthio having in each case up to 6 carbon atoms, or denotes cycloalkyl having 3 to 6 carbon atoms, $R^2$, $R^5$ and $R^6$ are identical or different and denote hydrogen, hydroxyl, nitro, cyano, formyl or halogen, or denote straight-chain or branched alkyl, alkenyl, alkinyl, alkoxy or alkylthio having in each case up to 8 carbon atoms, which are optionally substituted up to 3 times in an identical or different manner by hydroxyl, cyano, halogen, carboxyl, straight-chain or branched alkoxy, acyl or alkoxycarbonyl having in each case up to 6 carbon atoms, or by cycloalkyl having 3 to 6 carbon atoms, benzyl, phenyl, phenoxy, benzoyl or by a 5- to 7-membered, saturated or unsaturated heterocyclic radical having up to 3 hetero atoms from the series comprising S, N and O, it being possible for the cyclic radicals in turn to be substituted up to 2 times in an identical or different manner by trifluoromethyl, trifluoromethoxy, halogen, nitro, cyano, hydroxyl, hydroxymethyl or by straight-chain or branched alkyl or alkoxy having in each case up to 6 carbon atoms, or denote straight-chain or branched acyl or alkoxycarbonyl having in each case up to 8 carbon atoms, phenoxycarbonyl, benzyloxycarbonyl or carboxyl, or denote tetrazolyl, which is optionally substituted by triphenylmethyl or by straight-chain or branched alkyl having up to 6 carbon atoms, which can in turn be substituted by cyano, halogen, carboxyl, phenoxycarbonyl, hydroxyl or by straight-chain or branched alkoxy or alkoxycarbonyl having in each case up to 6 carbon atoms, or denote a group of the formula

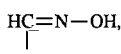

$-NR^9R^{10}$, $-CO-NR^{11}R^{12}$, $-CH_2-OR^{13}$ or $-S(O)_a-R^{14}$ wherein $R^9$, $R^{10}$, $R^{11}$ and $R^{12}$ are identical or different and denote hydrogen, cycloalkyl having 3 to 8 carbon atoms or straight-chain or branched alkyl having up to 8 carbon atoms, which is optionally substituted by phenyl, or $R^9$ and $R^{10}$, together with the nitrogen atom, form a 5- to 7-membered, saturated heterocyclic radical having up to 2 further hetero atoms from the series comprising S, N and O, $R^{13}$ denotes straight-chain or branched acyl having up to 6 carbon atoms or benzoyl, $R^{14}$ denotes straight-chain or branched alkyl having up to 8 carbon atoms, a denotes a number 1 or 2, $R^3$ and $R^7$ are identical or different and denote hydrogen, hydroxyl, carboxyl, straight-chain or branched alkoxy or alkoxycarbonyl having in each case up to 8 carbon atoms, or denote a group of the formula $-NR^{15}R^{16}$, wherein $R^{15}$ and $R^{16}$ have the abovementioned meaning of $R^9$ and $R^{10}$ and are identical to or different from these, or denote aryl having 6 to 10 carbon atoms, which is optionally substituted up to 2 times in an identical or different manner by trifluoromethyl, trifluoromethoxy, halogen, nitro, cyano, hydroxyl, hydroxymethyl or by straight-chain or branched alkyl or alkoxy having in each case up to 6 carbon atoms, or denote straight-chain or branched alkyl or alkenyl having in each case up to 8 carbon atoms, which is optionally substituted up to 3 times in an identical or different manner by hydroxyl, cyano, halogen, carboxyl, straight-chain or branched alkoxy, acyl or alkoxycarbonyl having in each case up to 6 carbon atoms, or by cycloalkyl having 3 to 6 carbon atoms, benzyl, phenyl, phenoxy, benzoyl or by a 5- to 7-membered, saturated or unsaturated heterocyclic radical having up to 3 hetero atoms from the series comprising S, N and O, it being possible for the cyclic radicals in turn to be substituted up to 2 times in an identical or different manner by trifluoromethyl, trifluoromethoxy, halogen, nitro, cyano, hydroxyl, hydroxymethyl or by straight-chain or branched alkyl or alkoxy having in each case up to 6 carbon atoms, $R^4$ denotes hydrogen, nitro, carboxyl or straight-chain or branched alkoxycarbonyl having up to 8 carbon atoms, or denotes a group of the formula —$NR^{17}R^{18}$, wherein $R^{17}$ and $R^{18}$ have the abovementioned meaning of $R^9$ and $R^{10}$ and are identical to or different from these, or denotes straight-chain or branched alkyl or alkenyl having in each case up to 8 carbon atoms, which is optionally substituted up to 3 times in an identical or different manner by hydroxyl, cyano, halogen, carboxyl, straight-chain or branched alkoxy, acyl or alkoxycarbonyl having in each case up to 6 carbon atoms, or by cycloalkyl having 3 to 6 carbon atoms, benzyl, phenyl, phenoxy, benzoyl or by a 5- to 7-membered, saturated or unsaturated heterocyclic radical having up to 3 hetero atoms from the series comprising S, N and O, it being possible for the cyclic radicals in turn to be substituted up to 2 times in an identical or different manner by trifluoromethyl, trifluoromethoxy, halogen, nitro, cyano, hydroxyl, hydroxymethyl or by straight-chain or branched alkyl or alkoxy having in each case up to 6 carbon atoms, $R^8$ has the abovementioned meaning of $R^1$ and $R^4$ and is identical to or different from these, D represents the >C=O group or represents a group of the formula >CH—T, wherein T denotes hydrogen or straight-chain or branched alkyl having up to 8 carbon atoms, E represents hydrogen, halogen, cyano, nitro, trifluoromethyl, hydroxyl, trifluoromethoxy or sunido, or represents straight-chain or branched alkyl, alkoxy or alkoxycarbonyl having in each case up to 6 carbon atoms, L represents a radical of the formula

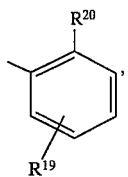

wherein $R_{19}$ has the abovementioned meaning of E and is identical to or different from this, and $R^{20}$ denotes a group of the formula —CO—$R^{21}$, —$SO_2R^{22}$, —CO—$NR^{23}R^{24}$, —NH—$SO_2R^{25}$ or —$SO_2$—$NR^{26}R^{27}$, wherein $R^{21}$ denotes hydroxyl or straight-chain or branched alkoxy having up to 6 carbon atoms, $R^{22}$ denotes hydroxyl, trifluoromethyl, straight-chain or branched alkoxy or alkyl having in each case up to 6 carbon atoms, phenyl or benzyl, which can optionally be substituted up to 2 times in an identical or different manner by halogen, trifluoromethyl or straight-chain or branched alkyl having up to 4 carbon atoms, $R^{23}$ and $R^{24}$ are identical or different and have the abovementioned meaning of $R^9$ and $R^{10}$ or $R^{23}$ denotes hydrogen and $R^{24}$ denotes the group —$SO_2R^{22}$, wherein $R^{22}$ has the abovementioned meaning, $R^{25}$ has the abovementioned meaning of $R^{22}$ and is identical to or different from this, $R^{26}$ and $R^{27}$ have the abovementioned meaning of $R^9$ and $R^{10}$ and are identical to or different from these, or $R^{26}$ denotes straight-chain or branched alkyl having up to 4 carbon atoms or hydrogen and $R^{27}$ has the abovementioned meaning of $R^{22}$ and is identical to or different from this or $R^{20}$ denotes a radical of the formula

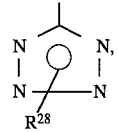

wherein $R^{28}$ denotes hydrogen or straight-chain or branched alkyl having up to 8 carbon atoms, which is optionally substituted by straight-chain or branched acyl having up to 6 carbon atoms, or denotes the triphenylmethyl group, and salts thereof.

The substituted pyridines and 2-oxo-1,2-dihydropyridines according to the invention can also be in the form of their salts. Salts with organic or inorganic bases or acids may be mentioned in general here.

Physiologically acceptable salts are preferred in the context of the present invention. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal salts or ammonium salts of the compounds according to the invention which possess a free carboxyl group or a tetrazolyl radical. Particularly preferred salts are, for example, those of sodium, potassium, magnesium or calcium, and ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which are either mirror images of one another (enantiomers) or are not (diastereomers). The invention relates both to the enantiomers or diastereomers and to particular mixtures thereof. The racemic forms, like the diastereomers, can be separated into the stereoisomerically uniform constituents in a known manner [compare E. L. Eliel, Stereochemistry of Carbon Compounds, McGraw Hill, 1962].

A heterocyclic radical in general represents a 5- to 7-membered, preferably 5- to 6-membered, saturated or unsaturated ring which can contain up to 2 oxygen, sulphur and/or nitrogen atoms as hereto atoms. 5- and 6-membered rings with one oxygen, sulphur and/or up to 2 nitrogen atoms are preferred. Rings which may be mentioned as preferred are: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl, piperazinyl or tetrazolyl.

A 5- to 6-membered, saturated heterocyclic radical which furthermore can contain up to 2 oxygen, sulphur and/or nitrogen atoms as hetero atoms in general represents azetidinyl, piperidyl, morpholinyl, piperazinyl or pyrrolidyl. Morpholinyl is preferred.

Preferred compounds of the general formula (I) are those in which

A represents a radical of the formula

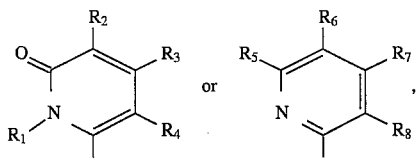

or wherein $R^1$ denotes hydrogen or straight-chain or branched alkyl having in each case up to 8 carbon atoms, which is optionally substituted by cyclopropyl, cyclopentyl, cyclohexyl, hydroxyl or by straight-chain or branched alkoxy or alkylthio having in each case up to 4 carbon atoms, or denotes cyclopropyl, cyclopentyl or cyclohexyl, $R^2$, $R^5$ and $R^6$ are identical or different and denote hydrogen, hydroxyl, nitro, cyano, formyl, fluorine, chlorine, bromine or iodine, or denote straight-chain or branched alkyl, alkenyl, alkinyl, alkoxy or alkylthio having in each case up to 6 carbon atoms, which are optionally substituted by hydroxyl, cyano, fluorine, chlorine, bromine, carboxyl, straight-chain or branched alkoxy, acyl or alkoxycarbonyl having in each case up to 4 carbon atoms, or by benzyl, phenyl, phenoxy, benzoyl or thienyl, it being possible for the cyclic radicals in turn to be substituted by trifluoromethoxy, trifluoromethyl, hydroxy methyl, fluorine, chlorine, bromine, iodine or by straight-chain or branched alkyl or alkoxy having in each case up to 6 carbon atoms, or denote straight-chain or branched acyl or alkoxycarbonyl having in each case up to 6 carbon atoms, phenoxycarbonyl, benzyloxy carbonyl or carboxyl, or denote tetrazolyl, which is optionally substituted by triphenylmethyl or by straight-chain or branched alkyl having up to 5 carbon atoms, which can in turn be substituted by cyano, fluorine, chlorine, bromine, carboxyl, hydroxyl or by straight-chain or branched alkoxy or alkoxycarbonyl having in each case up to 4 carbon atoms, or denote a group of the formula

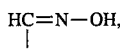

$-NR^9R^{10}$, $-CO-NR^{11}R^{12}$, $-CH_2-OR^{13}$ or $-S(O)_a-R^{14}$ wherein $R^9$, $R^{10}$, $R^{11}$ and $R^{12}$ are identical or different and denote hydrogen, cyclopropyl, cyclopentyl, cyclohexyl or straight-chain or branched alkyl having up to 6 carbon atoms, which is optionally substituted by phenyl, or $R^9$ and $R^{10}$, together with the nitrogen atom, form a morpholine ring, $R^{13}$ denotes straight-chain or branched acyl having up to 6 carbon atoms or benzoyl, $R^{14}$ denotes straight-chain or branched alkyl having up to 6 carbon atoms, a denotes a number 1 or 2, $R^3$ and $R^7$ are identical or different and denote hydrogen, hydroxyl, carboxyl or straight-chain or branched alkoxy or alkoxycarbonyl having in each case up to 6 carbon atoms, or denote a group of the formula $-NR^{15}R^{16}$, wherein $R^{15}$ and $R^{16}$ have the abovementioned meaning of $R^9$ and $R^{10}$ and are identical to or different from these, or denote phenyl, which can optionally be substituted by trifluoromethoxy, trifluoromethyl, hydroxymethyl, fluorine, chlorine, bromine, iodine or by straight-chain or branched alkyl or alkoxy having in each case up to 6 carbon atoms, or denote straight-chain or branched alkyl or alkenyl having in each case up to 6 carbon atoms, which are optionally substituted by hydroxyl, cyano, fluorine, chlorine, bromine, carboxyl, straight-chain or branched alkoxy, acyl or alkoxycarbonyl having in each case up to 4 carbon atoms, or by benzyl, phenyl, phenoxy, benzoyl or thienyl, it being possible for the cyclic radicals in turn to be substituted by trifluoromethoxy, trifluoromethyl, hydroxymethyl, fluorine, chlorine, bromine, iodine or by straight-chain or branched alkyl or alkoxy having in each case up to 6 carbon atoms, $R^4$ denotes hydrogen, nitro, carboxyl or straight-chain or branched alkoxycarbonyl having up to 6 carbon atoms, or denotes a group of the formula $-NR^{17}R^{18}$, wherein $R^{17}$ and $R^{18}$ have the abovementioned meaning of $R^9$ and $R^{10}$ and are identical to or different from these, or denotes straight-chain or branched alkyl or alkenyl having in each case up to 6 carbon atoms, which are optionally substituted by hydroxyl, cyano, fluorine, chlorine, bromine, carboxyl, straight-chain or branched alkoxy, acyl or alkoxycarbonyl having in each case up to 4 carbon atoms, or by benzyl, phenyl, phenoxy, benzoyl or thienyl, it being possible for the cyclic radicals in turn to be substituted by trifluoromethoxy, trifluoromethyl, hydroxymethyl, fluorine, chlorine, bromine, iodine or by straight-chain or branched alkyl or alkoxy having in each case up to 6 carbon atoms, $R^8$ has the abovementioned meaning of $R^1$ and $R^4$ and is identical to or different from these, D represents the $>C=O$ group or represents a group of the formula $>CH-T$, wherein T denotes hydrogen or straight-chain or branched alkyl having up to 7 carbon atoms, E represents hydrogen, fluorine, chlorine, bromine, cyano, nitro, methoxy, amido, trifluoromethyl or trifluoromethoxy, or represents straight-chain or branched alkyl or alkoxycarbonyl having in each case up to 4 carbon atoms, L represents a radical of the formula

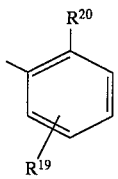

wherein $R^{19}$ has the abovementioned meaning of D and is identical to or different from this and $R^{20}$ denotes a group of the formula —CO—$R^{21}$, —SO$_2$$R^{22}$, —CO—NR$^{23}$R$^{24}$, —NH—SO$_2$R$^{25}$ or —SO$_2$—NR$^{26}$R$^{27}$, wherein $R^{21}$ denotes hydroxyl or straight-chain or branched alkoxy having up to 4 carbon atoms, $R^{22}$ denotes straight-chain or branched alkyl having up to 4 carbon atoms, benzyl, trifluoromethyl or p-tolyl, $R^{23}$ and $R^{24}$ are identical or different and have the abovementioned meaning of $R^9$ and $R^{10}$ or $R^{23}$ denotes hydrogen and $R^{24}$ denotes the group —SO$_2$R$^{22}$, wherein $R^{22}$ has the abovementioned meaning, $R^{25}$ has the abovementioned meaning of $R^{22}$ and is identical to or different from this, $R^{26}$ and $R^{27}$ have the abovementioned meaning of $R^9$ and $R^{10}$ and are identical to or different from these, or $R^{26}$ denotes straight-chain or branched alkyl having up to 4 carbon atoms or hydrogen and $R^{27}$ has the abovementioned meaning of $R^{22}$ and is identical to or different from this, or $R^{20}$ denotes a radical of the formula

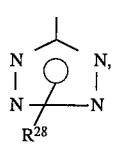

wherein $R^{28}$ denotes hydrogen or straight-chain or branched alkyl having up to 6 carbon atoms, which is optionally substituted by straight-chain or branched acyl having up to 4 carbon atoms, or denotes the triphenylmethyl group, and salts thereof.

Particularly preferred compounds of the general formula (I) are those in which

A represents a radical of the formula

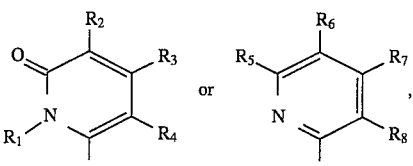

wherein $R^1$ denotes hydrogen or straight-chain or branched alkyl having up to 6 carbon atoms, which is optionally substituted by hydroxyl or straight-chain or branched alkoxy having in each case up to 3 carbon atoms, or denotes cyclopropyl, cyclopentyl or cyclohexyl, $R^2$ and $R^6$ are identical or different and denote hydrogen, cyano, formyl, fluorine, chlorine, bromine or iodine, or represent straight-chain or branched alkyl or alkoxy having in each case up to 4 carbon atoms, or denote straight-chain or branched alkoxy carbonyl having in each case up to 4 carbon atoms, phenoxycarbonyl, benzyloxycarbonyl or carboxyl, or denote tetrazolyl, which is optionally substituted by triphenylmethyl or by straight-chain or branched alkyl having up to 4 carbon atoms, or denote —NR$^9$R$^{10}$, —CO—NR$^{11}$R$^{12}$ or —CH$_2$—OR$^{13}$ wherein $R^9$, $R^{10}$, $R^{11}$ and $R^{12}$ are identical or different and denote hydrogen, cyclopropyl, cyclopentyl or straight-chain or branched alkyl having up to 4 carbon atoms, which is optionally substituted by phenyl, $R^{13}$ denotes straight-chain or branched acyl having up to 4 carbon atoms or benzoyl, $R^5$ denotes hydroxyl or straight-chain or branched alkyl or alkoxy having in each case up to 6 carbon atoms, $R^3$ and $R^7$ are identical or different and denote hydrogen, hydroxyl, carboxyl, straight-chain or branched alkoxy or alkoxycarbonyl having in each case up to 4 carbon atoms, or denote a group of the formula —NR$^{15}$R$^{16}$, wherein $R^{15}$ and $R^{16}$ have the abovementioned meaning of $R^9$ and $R^{10}$ and are identical to or different from these, or denote phenyl, vinyl or straight-chain or branched alkyl having up to 5 carbon atoms, $R^4$ denotes hydrogen, carboxyl or straight-chain or branched alkoxycarbonyl having up to 4 carbon atoms, or denotes a group of the formula —NR$^{17}$R$^{18}$, wherein $R^{17}$ and $R^{18}$ have the abovementioned meaning of $R^9$ and $R^{10}$ and are identical to or different from these, or denotes vinyl or straight-chain or branched alkyl having up to 4 carbon atoms, $R^8$ has the abovementioned meaning of $R^1$ and $R^4$ and is identical to or different from these, D represents the >C=O group or represents a group of the formula

wherein
T denotes hydrogen or straight-chain or branched alkyl having up to 5 carbon atoms, E represents hydrogen, fluorine, chlorine, bromine, cyano, methoxy, trifluoromethyl or straight-chain or branched alkyl or alkoxycarbonyl having in each case up to 3 carbon atoms and L represents a radical of the formula

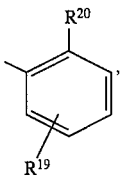

wherein
$R^{19}$ denotes hydrogen,
and
$R^{20}$ denotes a group of the formula $-CO-R^{21}$,
wherein
$R^{21}$ denotes hydroxyl or straight-chain or branched alkoxy having up to 4 carbon atoms,
or
$R^{20}$ denotes the tetrazolyl radical of the formula

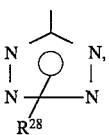

wherein
$R^{28}$ denotes hydrogen or straight-chain or branched alkyl having up to 4 carbon atoms,
or denotes the triphenylmethyl group,
and salts thereof.

Very particularly preferred compounds of the general formula (I) are those in which A represents a radical of the formula

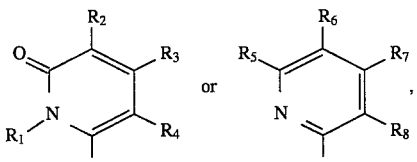

wherein
$R^1$ denotes straight-chain or branched alkyl having up to 4 carbon atoms, $R^2$ and $R^6$ are identical or different and denote hydrogen, carboxyl or straight-chain or branched alkoxycarbonyl having up to 4 carbon atoms, $R^5$ denotes hydroxyl or straight-chain or branched alkyl or alkoxy having up to 4 carbon atoms, $R^3$ and $R^7$ are identical or different and denote hydrogen, hydroxyl, carboxyl or straight-chain or branched alkoxy or alkoxycarbonyl having in each case up to 4 carbon atoms, $R^4$ denotes hydrogen, carboxyl or straight-chain or branched alkoxycarbonyl having up to 4 carbon atoms, $R^8$ has the abovementioned meaning of $R^1$ and $R^4$ and is identical to or different from these, D represents the

group or represents a group of the formula

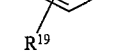

wherein
T denotes hydrogen or straight-chain or branched alkyl having up to 4 carbon atoms, E represents hydrogen, fluorine, chlorine, trifluoromethyl or cyano, and L represents a radical of the formula

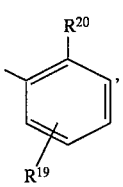

wherein
$R^{19}$ denotes hydrogen,
and
$R^{20}$ denotes a group of the formula $-CO-R^{21}$,
wherein
$R^{21}$ denotes hydroxyl or straight-chain or branched alkoxy having up to 4 carbon atoms,
or
$R^{20}$ denotes the tetrazolyl radical of the formula

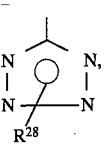

wherein
$R^{28}$ denotes hydrogen or the triphenylmethyl group,
and salts thereof.

A process has furthermore been found for the preparation of the compounds of the general formula (I) according to the invention, characterized in that compounds of the general formula (II)

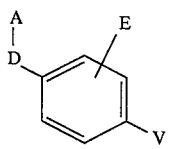
(II)

in which

A, D and E have the abovementioned meaning and

V represents a typical leaving group, such as, for example, bromine, iodine or methane-, toluene-, fluoro- or trifluoromethanesulphonyloxy, preferably bromine, are reacted with compounds of the general formula (III) or (IIIa)

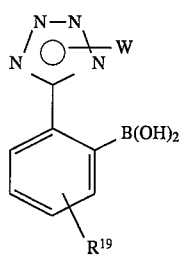
(III)

or

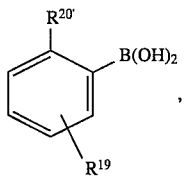
(IIIa)

in which $R^{19}$ has the abovementioned meaning,

W represents hydrogen or represents the triphenyl methyl group and $R^{20}$ has the abovementioned meaning of $R^{20}$ but does not represent the tetrazolyl radical, in inert solvents in the presence of a base and under metal catalysis, and in the case where W represents the triphenylmethyl group, this is then split off with acids in organic solvents and/or water under customary conditions, and, if appropriate, in the case of the radicals listed under the substituent $R^{20}$, the products are derivatized by customary methods, after hydrolysis of the particular esters, for example by amidation or sulphoamidation, and in the case of the salts, preferably starting from the free tetrazole ($R^{28}$/W=H), these are reacted with acids or bases, and in the case of the free acid $R^{20}$=$CO_2H$ and the free tetrazole $R^{28}$=H, the products are reacted with acids, starting from the salts, and, if appropriate, the other substituents are also varied at any process stage by known methods.

The process according to the invention can be illustrated by the following equation by way of example:

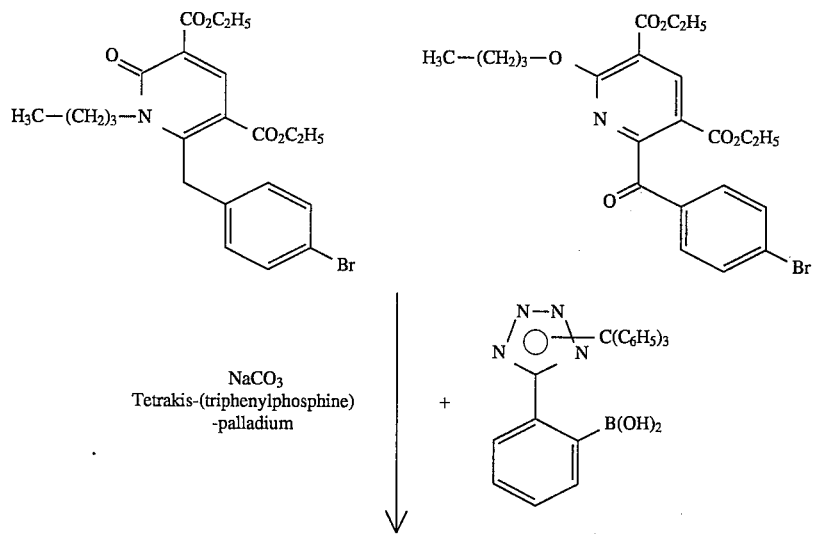

Suitable solvents for the process are the customary organic solvents which do not change under the reaction conditions. These include, preferably, water or alcohols, such as, for example, methanol, ethanol and propanol, ethers such as diethyl ether, dioxane, tetrahydrofuran or

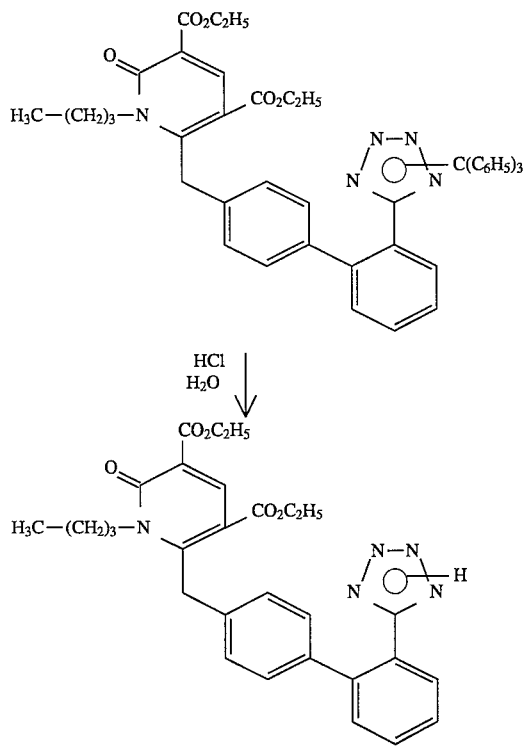
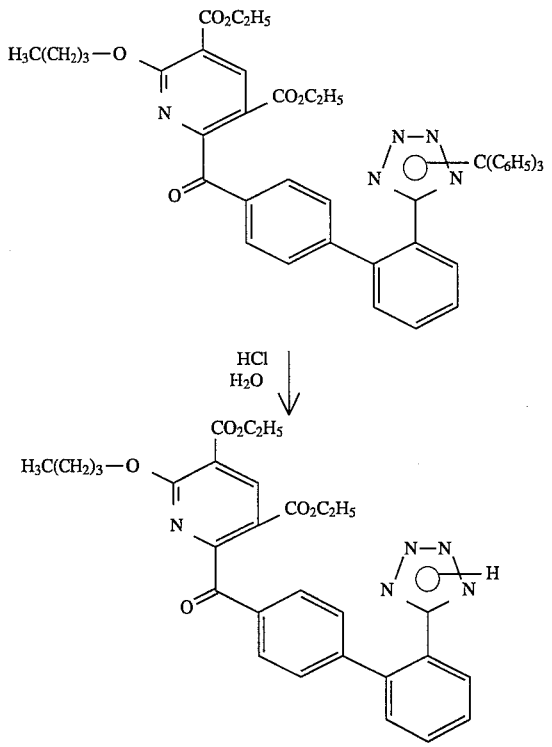

glycol dimethyl ether, or hydrocarbons such as benzene, toluene, xylene, hexane, cyclohexane or petroleum fractions, or halogenohydrocarbons such as methylene chloride, chloroform, carbon tetrachloride, dichloroethylene, trichloroethylene or chlorobenzene, or ethyl acetate, dimethyl sulphoxide, dimethylformamide or dimethoxyethane, hexamethylphosphoric acid triamide, acetonitrile, acetone or nitromethane. It is likewise possible to use mixtures of the solvents mentioned. Tetrahydrofuran, acetone, dimethylformamide, dimethoxyethane, toluene and methanol/water are preferred.

Bases which can be employed for the process according to the invention are in general inorganic or organic bases. These include, preferably, alkali metal hydroxides such as, for example, sodium hydroxide or potassium hydroxide alkaline earth metal hydroxides such as, for example, barium hydroxide, alkali metal carbonates such as sodium carbonate or potassium carbonate, alkaline earth metal carbonates such as calcium carbonate or caesium carbonate, or alkali metal or alkaline earth metal alcoholates or amides such as sodium methanolate or potassium methanolate, sodium ethanolate or potassium ethanolate or potassium tert-butylate, thalliumcarbonate or hydroxide, or lithium diisopropylamide (LDA), or organic amines (trialkyl($C_1$–$C_6$)amines such as triethylamine, or heterocyclic compounds, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium, or hydrides thereof such as sodium hydride, as bases. Potassium carbonate, sodium hydride, potassium tert-butylate, caesium carbonate, sodium carbonate or thallium hydroxide or carbonate are preferred.

The base is in general employed in an amount of 0.05 to 10 mol, preferably of 1 mol to 2 mol, in each case per mole of the compound of the formula (III).

The processes according to the invention are in general carried out in a temperature range from –100° C. to +150° C., preferably from 0° C. to 100° C., in an inert gas atmosphere. Suitable catalysts are in general metal complexes of nickel, palladium or platinum, preferably palladium(0) complexes such as, for example, tetrakistriphenylphosphinepalladium. It is likewise possible to employ phase transfer catalysts, such as, for example, tetra-n-butylammonium bromide or crown ethers.

The process according to the invention is in general carried out under normal pressure. However, it is also possible to carry out the process under increased pressure or under reduced pressure (for example in a range from 0.5 to 5 bar).

The triphenylmethyl group is eliminated with acetic acid or trifluoroacetic acid and water or one of the abovementioned alcohols or with aqueous hydrochloric acid in the presence of acetone and alcohols.

The elimination is in general carried out in a temperature range from 0° C. to 150° C. preferably from 20° C. to 100° C., under normal pressure.

The catalyst is employed in an amount of 0.005 mol to 0.2 mol, preferably of 0.01 mol to 0.05 mol, per mole of the compound of the general formula (II).

The alkylation is in general carried out with alkylating agents such as, for example, ($C_1$–$C_6$)-alkylhalides, sulphonic acid esters or substituted or unsubstituted ($C_1$–$C_6$)-dialkyl- or ($C_1$–$C_6$)-diarylsulphonates, preferably methyl iodide or dimethylsulphate.

The alkylation is in general carried out in one of the abovementioned solvents, preferably in dimethylformamide, in a temperature range from 0° C. to +70° C., preferably from 0° C. to +30° C., under normal pressure.

Suitable bases for the hydrolysis are the customary inorganic bases. These include, preferably, alkali metal hydroxides or alkaline earth metal hydroxides such as, for example, sodium hydroxide, potassium hydroxide or barium hydroxide, or alkali metal carbonates such as sodium carbonate or potassium carbonate or sodium bicarbonate, or alkali metal alcoholates such as sodium methanolate, sodium ethanolate, potassium methanolate, potassium ethanolate or potassium tert-butanolate. Sodium hydroxide or potassium hydroxide are particularly preferably employed.

Suitable solvents for the hydrolysis are water or the customary organic solvents for hydrolysis. These include, preferably, alcohols such as methanol, ethanol, propanol, isopropanol or butanol, or esters such as tetrahydrofuran or dioxane, or dimethylformamide or dimethyl sulphoxide. Alcohols such as methanol, ethanol, propanol or isopropanol, are particularly preferably used. It is likewise possible to employ mixtures of the solvents mentioned.

If appropriate, the hydrolysis can also be carried out with acids such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mol, preferably of 1 to 1.5 mol, per mole of the ester. Molar amounts of the reactants are particularly preferably used.

The hydrolysis of tert-butyl esters is in general carried out with acids, such as, for example, hydrochloric acid or trifluoroacetic acid, in the presence of one of the abovementioned solvents and/or water or mixtures thereof, preferably with dioxane or tetrahydrofuran.

The amidation and the sulphonamidation are in general carried out in one of the abovementioned solvents, preferably in tetrahydrofuran or methylene chloride.

If appropriate, the amidation and the sulphonamidation can proceed via the activated stage of the acid halides, which can be prepared from the corresponding acids by reaction with thionyl chloride, phosphorus trichloride, phosphorus pentachloride, phosphorus tribromide or oxalyl chloride.

The amidation and the sulphonamidation are in general carried out in a temperature range from −20° C. to +80° C., preferably from −10° C. to +30° C., under normal pressure.

Suitable bases for this are, in addition to the abovementioned bases, preferably triethylamine and/or dimethylaminopyridine, DBU or DABCO.

The base is employed in an amount of 0.5 mol to 10 mol, preferably of 1 mol to 2 mol, per mole of the corresponding acid or ester.

Acid-binding agents which can be employed for the sulphonamidation are alkali metal or alkaline earth metal carbonates such as sodium carbonate or potassium carbonate, alkali metal or alkaline earth metal hydroxides such as, for example, sodium hydroxide or potassium hydroxide, or organic bases such as pyridine, triethylamine, N-methylpiperidine or bicyclic amidines such as 1,5-diazabicyclo[3.4.0]-non-5-ene (DBN) or 1,5-diazabicyclo[3.4.0]undec-5-ene (DBU). Potassium carbonate is preferred.

Suitable dehydrating reagents are carbodiimides such as, for example, diisopropylcarbodiimide, dicyclohexylLe carbodiimide or N-(3-dimethylaminopropyl)-N'-ethylcarbodiimide hydrochloride, or carbonyl compounds such as carbonyldiimidazole, or 1,2-oxazolium compounds such as 2-ethyl-5-phenyl-1,2-oxazolium 3-sulphonate, or propanephosphoric anhydride or isobutyl chloroformate or benzotriazolyloxy-tris-(dimethylamino)phosphonium hexafluorophosphate or phosphonic acid diphenyl esteramide or methanesulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount of 0.5 to 3 mol, preferably of 1 to 1.5 mol, per mole of the corresponding carboxylic acids.

The compounds of the general formula (II) are new in most cases and can be prepared, for example, by a process in which in the case where A represents the radical of the formula

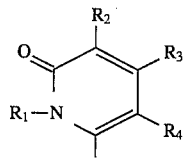

and D denotes the

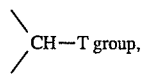

compounds of the general formula (IV)

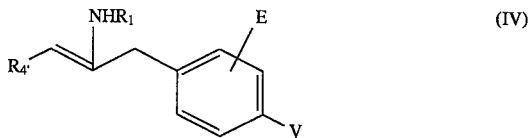

in which

R$^1$, E and V have the abovementioned meaning
and

R$^{4'}$ represents nitrile, or represents one of the chemically appropriate radicals mentioned above under R$^4$, preferably (C$_1$–C$_4$)-alkoxycarbonyl, nitro or nitrile, are reacted with compounds of the general formula (V)

in which

R$^{2'}$ and R$^{3'}$ are identical or different and represent nitrile, or represent one of the chemically appropriate radicals mentioned above under R$^2$ and R$^3$, preferably represent (C$_1$–C$_4$)-alkoxycarbonyl or nitrile, and X represents (C$_1$–C$_4$)-alkoxy or (C$_1$–C$_4$)-dialkylamino.

The reaction proceeds in a temperature range from +50° C. to +130° C., preferably from +70° C. to +110° C., under normal pressure.

The compounds of the general formula (IV) are known in some cases and can then be prepared, for example, by a process in which compounds of the general formula (VI)

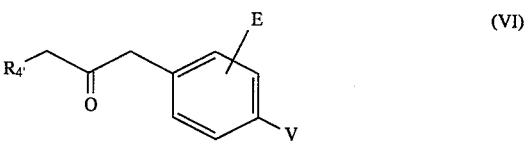

in which $R^{4'}$, E and V have the abovementioned meaning,
are reacted with ammonia ($R^1$=H) or with amines of the general formula (VII)

$$H_2N-R^1 \qquad \text{(VII)}$$

in which $R^1$ has the abovementioned meaning,
in one of the abovementioned solvents, preferably ethanol.

The reaction in general proceeds in a temperature range from −10° C. to +100° C., preferably from 0° C. to +100° C.

The amines of the general formula (VII) are known.

The compounds of the general formula (VI) are known in some cases and can be prepared, for example, by a process in which compounds of the general formula (VIII)

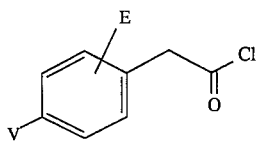

(VIII)

in which

E and V have the abovementioned meaning,
are reacted with compounds of the general formula (IX)

$$R^{4'}-CH_2-CO_2H \qquad \text{(IX)}$$

in which $R^{4'}$ has the abovementioned meaning,
in one of the abovementioned solvents, preferably tetrahydrofuran.

The reaction is carried out in a temperature range from 0° C. to +40° C., preferably at +20° C.

The compounds of the general formulae (VIII) and (IX) are known per se.

The compounds of the General formula (II) in which A represents the radical of the formula

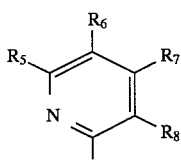

are new and can be prepared, for example, by a process in which compounds of the general formula (IIa)

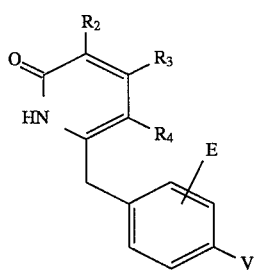

(IIa)

in which $R^2$, $R^3$, $R^4$, E and V have the abovementioned meaning,
are first reacted with compounds of the general formula (X)

$$R^1-Z \qquad \text{(X)}$$

in which $R^1$ has the abovementioned meaning, but preferably represents ($C_1-C_6$)-alkyl,
and Z represents halogen, preferably iodine,
in one of the abovementioned solvents, preferably dimethylformamide, in the presence of a base, preferably caesium carbonate.

The compounds of the general formula (II) in which D represents the C=O group furthermore are formed in this alkylation.

The reaction is in general carried out in a temperature range from 0° C. to +50° C., preferably from +10° C. to +30° C., under normal pressure.

The base is employed in an amount of 1 mol to 10 mol, preferably of 1 mol to 3 mol, per mole of the compounds of the general formula (X).

The compounds of the general formula (IIa) are new and can be prepared as described above.

The compounds of the general formula (X) are known.

The compounds of the general formula (III) are known in some cases or, in the case where W=H, are new and can then be prepared by a process in which phenyltetrazole is first reacted in an aprotic solvent and in the presence of a base under an inert gas atmosphere, trimethyl borate is then added and, in a last step, the product is hydrolysed with acids.

Suitable solvents for the process are aprotic solvents such as ethers, for example tetrahydrofuran, diethyl ether, toluene, hexane or benzene. Tetrahydrofuran is preferred.

Suitable bases are prim-, sec- and tert-butyllithium and phenyllithium. n-Butyllithium is preferred.

The base is employed in an amount of 2 mol to 5 mol, preferably of 2 mol to 3 mol, per mole of phenyltetrazole.

Suitable acids are in general mineral acids, such as, for example, hydrochloric acid, or $C_1-C_4$-carboxylic acids, such as, for example, acetic acid, or phosphoric acids. Hydrochloric acid is preferred.

The acid is in general employed in an amount of 1 mol to 10 mol, preferably of 1 mol to 3 mol.

The process is in general carried out in a temperature range from −70° C. to +25° C., preferably at −10° C. to 0° C.

The process according to the invention is in general carried out under normal pressure. However, it is also possible to carry out the process under increased pressure or under reduced pressure (for example in a range from 0.5 to 5 bar).

The compounds of the general formula (IIIa) are new in some cases or can be prepared by customary methods.

The above preparation processes are mentioned merely for illustration. The preparation of the compounds of the general formula (I) according to the invention is not limited to these processes, and any modification of these processes can be used in the same manner for the preparation.

The substituted pyridines and 2-oxo-1,2-dihydropyridines according to the invention display an unforeseeable, valuable pharmacological action spectrum.

The compounds according to the invention have a specific A II-antagonistic action, since they competitively inhibit bonding of angiotensin II to the receptors. They suppress the vasoconstrictory and aldosterone secretion-stimulating effects of angiotensin II. They furthermore inhibit the proliferation of smooth muscle cells.

They can therefore be employed in medicaments for the treatment of arterial hypertension and atherosclerosis. They can moreover be employed for the treatment of coronary heart diseases, cardiac insufficiency, disturbances in cerebral performance, ischaemic cerebral diseases, disturbances in peripheral circulation, dysfunctions of the kidney and adrenal gland, bronchospastic and vascular-related diseases of the respiratory passages, sodium retention and oedemas.

The compounds can also be used for the control of glaucoma, diabetic retinopathy and increases in the mobility of the intraocular retinal fluid.

They are also suitable for controlling diseases of the central nervous system such as for example depression, migraine, schizophrenia or anxiety states, brain dysfunctions, strokes, diabetic nephropathy, cardiac dysrhythmias, or for the prophylaxis of coronary heart diseases or restenosis after angioplasty and vascular surgery.

Investigation of the inhibition of contraction induced with agonists

Rabbits of both sexes are stunned by a blow to the neck and exsanguinated, or alternatively anaesthetized with Nembutal (about 60–80 mg/kg i.v.) and sacrificed by opening the thorax. The thoracic aorta is removed, freed from adhering connective tissue and divided into annular segments 1.5 mm wide, which are introduced individually, under an initial load of about 3.5 g, into 10 ml organ baths containing carbogen-gassed Krebs-Henseleit nutrient solution, temperature-controlled at 37° C., of the following composition: 119 mmol/l of NaCl; 2.5 mmol/l of $CaCl_2 \times 2\ H_2O$; 1.2 mmol/l of $KH_2PO_4$; 10 mmol/l of glucose; 4.8 mmol/l of KCl; 1.4 mmol/l of $MgSO_4 \times 7\ H_2O$ and 25 mmol/l of $NaHCO_3$.

The contractions are recorded isometrically by Statham UC2 cells via bridge amplifiers (from Mulheim or DSM Aalen) and digitalized and evaluated by means of A/D converters (system 570, Keithley Munich). The agonist dose/effect curves (DEC) are plotted hourly. With each DEC, 3 or 4 individual concentrations are introduced into the baths at intervals of 4 minutes. The end of the DEC and subsequent washing-out cycles (16 times for in each case about 5 seconds/minute with the abovementioned nutrient solution) is followed by a 28-minute resting or incubation phase, within which the contractions as a rule reach the starting value again.

The height of the 3rd DEC in the normal case is used as a reference parameter for evaluation of the test substance to be investigated in subsequent passes, this being introduced into the baths during the subsequent DECs at the start of the incubation time in a dosage which increases each time. Each aortic ring is stimulated the whole day with always the same agonist.

| Agonists and their standard concentrations – application volume per individual dose = 100 ml): | | |
| --- | --- | --- |
| KCl | 22.7; 32.7; 42.7; 52.7 | mmol/l |
| Noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$ | g/ml |
| Methoxamine | $10^{-7}$; $10^{-6}$; $10^{-5}$ | g/ml |
| Angiotensin II | $3 \times 10^{-9}$; $10^{-8}$; $3 \times 10^{-8}$; $10^{-7}$ | g/ml |

The effect in each case at the 3rd=submaximum agonist concentration is taken as a basis for calculation of the $IC_{50}$ (concentration at which the substance to be investigated causes 50% inhibition).

The compounds according to the invention inhibit the angiotensin II-induced contraction of the isolated rabbit aorta as a function of the dose. The contraction induced by potassium depolarization or other agonists was not inhibited or was inhibited only weakly at high concentrations.

Blood pressure measurements on rats infused with angiotensin II

Male Wistar rats (Moellegaard, Copenhagen, Denmark) with a body weight of 300–350 g are anaesthetized with thiopental (100 mg/kg i.p.). After tracheotomy, a catheter for blood pressure measurement is inserted into the femoral artery and a catheter for angiotensin II infusion and a catheter for administration of the substance are inserted into the femoral veins. After administration of the ganglionic blocker pentolinium (5 mg/kg i.v.), the angiotensin II infusion (0.3 μg/kg/minute) is started. As soon as the blood pressure values have reached a stable plateau, the test substances are administered either intravenously, or orally as a suspension or solution in 0.5% Tylose. The changes in blood pressure under the influence of the substance are stated as mean values±SEM in the table.

Determination of the antihypertensive activity on conscious hypertensive rats

The oral antihypertensive activity of the compounds according to the invention was tested on conscious rats with surgically inducedunilateral renal arteriostenosis. For this, the right renal artery was constricted with a silver clip of 0.18 mm internal diameter. With this form of hypertension, the plasma renin activity is increased in the first six weeks after the intervention.

The arterial blood pressure of these animals was measured bloodlessly using a "tail cuff" at defined intervals of time after administration of the substance. The substances to be tested were administered intragastrally ("orally") by a stomach tube in various doses as a suspension in a Tylose suspension. The compounds according to the invention lower the arterial blood pressure of the hypertensive rats in a clinically relevant dosage.

The compounds according to the invention furthermore inhibit specific bonding of radioactive angiotensin II as a function of the concentration.

Interaction of the compounds according to the invention with the angiotensin II receptor on membrane fractions from the adrenal cortex (bovine)

Bovine adrenal cortices (AC) which are freshly removed and carefully freed from the capsula medulla are comminuted to a coarse membrane homogenate in sucrose solution (0.32M) with the aid of an Ultra-Turrax (Janke & Kunkel, Staufen, Bavariz) and partly purified to membrane fractions in two centrifugation steps.

The investigations on receptor binding are carried out on partly purified membrane fractions of bovine AC using radioactive angiotensin II in an assay volume of 0.25 ml which contains, specifically, the partly purified membranes (50–80 μg), $^3H$-angiotensin II (3–5 nM), test buffer solution (50 mM Tris, pH 7.2), 5 mM $MgCl_2$ and the substances to be investigated. After an incubation time of 60 minutes at room temperature, the non-bound radioactivity of the samples is separated by means of moistened glass fibre filters (Whatman GF/C) and the bound radioactivity is measured spectrophotometrically in a scintillation cocktail, after washing the protein with ice-cold buffer solution (50 mM Tris/HCl, pH 7.4, 5% PEG 6000). The raw data were analysed with computer programs to $K_i$ and $IC_{50}$ values ($K_i$: $IC_{50}$ values corrected for the radioactivity used; $IC_{50}$ values: concentration at which the substance to be investigated causes 50% inhibition of the specific binding of the radio ligand).

Investigation of the inhibition of the proliferation of smooth muscle cells by the compounds according to the invention Smooth muscle cells which are obtained from the aortas of rats by the media-explantate technique are used to determine the antiproliferative action of the compounds [R. Ross, J. Cell. Biol. 50, 172, 1971]. The cells are sown in suitable culture dishes, as a rule 96-hole plates, and cultured for 2–3 days in medium 199 with 7.5% of FCS and 7.5% of NCS, 2 mM L-glutamine and 15 mM HEPES, pH 7.4 in 5% of $CO_2$ at 37° C. Thereafter, the cells are synchronized by serum withdrawal for 2–3 days and then stimulated to growth with serum or other factors. At the same time, test compounds are added. After 16–20 hours, 1 μCi of $^3$H-thymidine is added, and after a further 4 hours, the incorporation of this substance into the DNA of the cells which can be precipitated with TCA is determined. The active compound concentration which causes half the maximum inhibition of the thymidine incorporation caused by 10% of FCS on sequential dilution of the active compound is calculated for determination of the $IC^{50}$ values.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Administration is effected in the customary manner, preferably orally or parenterally, in particular perlingually or intravenously.

In the case of parenteral use, solutions of the active compound can be employed, using suitable liquid excipient materials.

In general, it has proved advantageous in the case of intravenous administration to administer amounts of about 0.001 to 1 mg/kg, preferably about 0.01 to 0.5 mg/kg of body weight to achieve effective results, and in the case of oral administration, the dosage is about 0.01 to 20 mg/kg, preferably 0.1 to 10 mg/kg of body weight.

Nevertheless, it may be necessary to deviate from the amounts mentioned, and in particular as a function of the body weight and the nature of the administration route, or of the behaviour of the individual towards the medicament, the nature of its formulation and the time or interval at which administration takes place. Thus in some cases it may be sufficient to manage with less than the abovementioned minimum amount, while in other cases the upper limit mentioned must be exceeded. Where relatively large amounts are administered, it may be advisable to divide these into a plurality of individual doses over the course of the day.

Starting compounds

EXAMPLE I

Ethyl 4-(4-bromophenyl)-3-oxo-butanoate

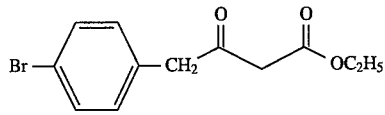

1 l (2 mol) of a 2M solution of isopropylmagnesium chloride in tetrahydrofuran is added dropwise to a solution of 125 g (0.95 mol) of malonic acid monoethyl ester in 1 l of tetrahydrofuran at 0° C. and the mixture is stirred at 20° C. for 1 hour. 146 g (0.63 mol) of 4-bromophenylacetyl chloride are then added dropwise at 20° C., and the reaction mixture is stirred at this temperature for 2 hours and brought to pH=3 with 1N hydrochloric acid. It is stirred overnight, the phases are separated, the aqueous phase is washed with diethyl ether, the combined organic phases are washed with water and aqueous sodium bicarbonate solution, the solvent is distilled off, the residue is dissolved in methylene chloride, the solution is dried with sodium sulphate and filtered over silica gel using methylene chloride and the solvent is removed on a rotary evaporator.

Crude yield: 167.9 g of an oil, 93.5% of theory $R_f$ (petroleum ether/ethyl acetate 5:1, silica gel)=0.43

EXAMPLE II

Ethyl 3-amino-4-(4-bromophenyl)-but-2-enoate
Ammonia is

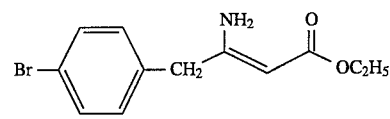

passed into a solution of 10 g (35 mmol) of the compound from Example I in 200 ml of ethanol at 0° C. for 3 hours and the solution is warmed to 20° C. overnight. The solvent is distilled off in vacuo, the residue is dissolved in methylene chloride and the solution is filtered over silica gel. After removal of the solvent, 7.8 g of the title compound are obtained.

Yield: 78% of theory MS (EI): 283/285 (M), 284/286 (M+I), 237, 239

EXAMPLE III

Diethyl 6-(4-bromobenzyl)-2-oxo-1,2-dihydropyridine-2,5-dicarboxylate

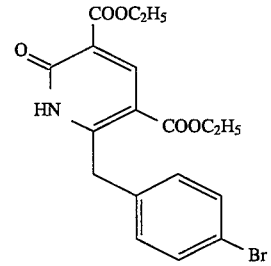

69 g (0.24 mol) of the compound from Example II and 52.49 g (0.24 mol) of diethyl ethoxymethylenemalonate are stirred at 100° C. for 70 hours. The reaction mixture is absorbed on 250 g of silica gel and eluted with ethyl acetate/petroleumether mixtures (1:10–1:0) on 200 g of silica gel. The resulting brown solid [$R_f$ (ethyl acetate/petroleum ether 1:1, silica gel)=0.28] is titrated with petroleum ether and ethyl acetate/petroleum ether (1:10) and dried over phosphorus pentoxide in vacuo to give 18.3 g of the title compound.

Yield: 18.5% of theory MS 407, 409 ($M^+$)

EXAMPLE IV

Diethyl 6-butoxy-2-(4-bromophenylcarbonyl)-pyridine-3,5-dicarboxylate

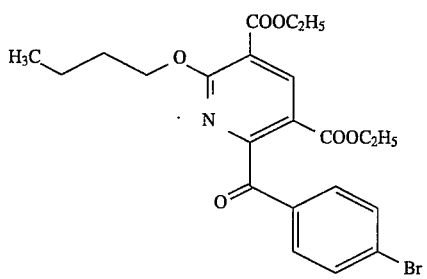

A suspension of 1 g (2.45 mmol) of the compound from Example III, 2.8 ml (4.5 mmol) of n-butyl iodide and 3.99 g (12.25 mmol) of caesium carbonate in 20 ml of dimethylformamide is stirred overnight at 20° C. The reaction mixture is partitioned between water and ethyl acetate, the organic phase is washed with water and saturated sodium chloride solution and dried over sodium sulphate and the resulting crude oil (2.3 g) is chromatographed over 300 g of silica gel using ethyl acetate/petroleum ether 1:20 to give 0.13 g of the title compound.

Yield: 11.1% of theory $R_f$ (silica gel, ethyl acetate/petroleum ether 1:10)=0.25 MS=477, 479 (M$^+$) 0.26 g of

EXAMPLE V

5-Butyl 3-ethyl 6-butoxy-2-(4-bromophenylcarbonyl)pyridine-3,5-dicarboxylate

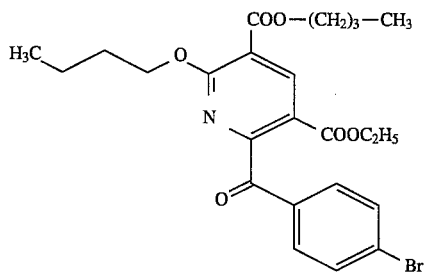

Yield: 21% of theory $R_f$ (silica gel, ethyl acetate/petroleum ether 1:10)=0.33 MS 505, 507 (M$^+$) and 93 mg of

EXAMPLE VI

Diethyl 6-butoxy-2-[1-(bromophenyl-4-yl)-pentyl]-pyridine-3,5-dicarboxylate

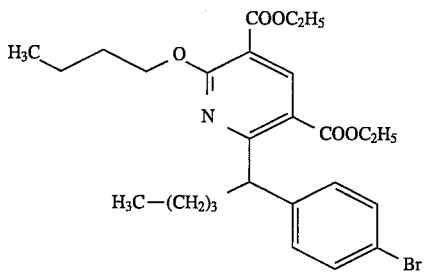

are furthermore obtained.

Yield: 7.3% of theory $R_f$ (silica gel, ethyl acetate/petroleum ether 1:10)=0.49 MS 519, 521 (M$^+$)

EXAMPLE VII 2-(Tetrazol-5'-yl)phenylboronic acid

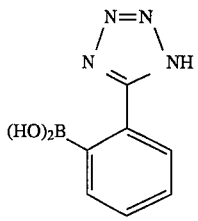

17.6 ml (44 mmol) of a 2.5M solution of n-butyllithium in n-hexane are added to a solution of 2.9 g (20 mmol) of 5-phenyltetrazole in 50 ml of tetrahydrofuran at –5° C. under argon. The mixture is stirred at –5° C. to 0° C. for 30 minutes and 10 ml (88 mmol) of trimethyl borate are added at this temperature. The cooling bath is then removed and 10 ml of half-concentrated hydrochloric acid are added to the solution at room temperature. After 1 hour, the mixture is extracted with 100 ml of ethyl acetate, the organic phase is separated off and the aqueous phase is extracted twice with 20 ml of ethyl acetate each time. The combined organic phases are dried over sodium sulphate and concentrated and the residue is purified over silica gel using toluene/glacial acetic acid/methanol (38:0.1:2).

Yield: 2.65 g (70% of theory) $R_f$=0.26 (toluene/methanol/glacial acetic acid=32:8:1)

$^{13}$C-NMR: δ=156.7; 137.9; 133.5; 129.8; 128.9; 127.7; 126.9 ppm.

EXAMPLE VIII

Ethyl 3-butylamino-4-(4-bromophenyl)-but-2-enoate

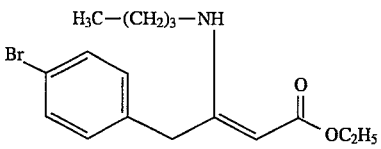

A solution of 50 g (0.175 mol) of the compound from Example I and 19 ml (0.195 mol) of n-butylamine in 500 ml of ethanol is heated under reflux overnight. After concentration, 54.3 g of the title compound are obtained as an oil.

Crude yield: 91.2% of theory $R_f$ (silica gel, petroleum ether/ethyl acetate 10:1)=0.52

EXAMPLE IX

Diethyl 1-butyl-2-oxo-6-(4-bromophenyl-ylmethyl)-1,2-dihydropyridine-3,5-dicarboxylate

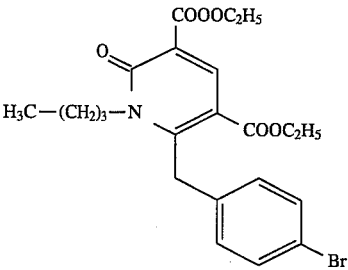

The title compound is obtained analogously to Example III starting from the compound from Example VIII.

$R_f$ (silica gel, toluene/ethyl acetate 10:1)=0.14

EXAMPLE X

Methyl 4-(4-bromophenyl)-3-oxo-butanoate

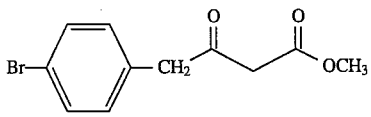

The title compound is obtained analogously to the instructions of Example I from malonic acid monomethyl ester.

Yield: 80% of theory $R_f$ (petroleum ether/ethyl acetate 5:1, silica gel)=0.38

EXAMPLE XI

Methyl 3-butylamino-4-(4-bromophenyl)-but-2-enoate

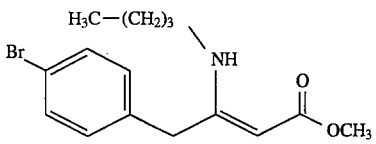

The title compound is obtained analogously to the instructions of Example VIII starting from the compound from Example X.

Yield: 78.8% of theory $R_f$ (petroleumether/ethyl acetate 5:1, silica gel)=0.63

EXAMPLE XII

3-Ethyl 5-methyl 1-butyl-2-oxo-6-(4-bromophenyl-yl-methyl)-1,2-dihydropyridine-3,5-dicarboxylate

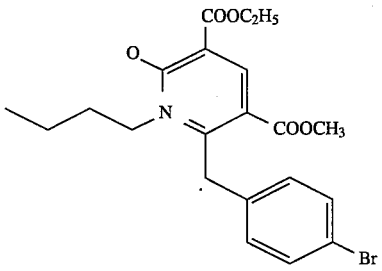

The title compound is obtained analogously to the instructions of Example IX starting from the compound from Example XI.

Yield: 65% of theory $R_f$ (petroleumether/ethyl acetate 2:1, silica gel)=0.44

PREPARATION EXAMPLES

EXAMPLE 1

Diethyl 6-butoxy-2-[2'-(2-triphenylmethyl-tetrazol-5-yl)biphenyl-4-carbonyl]-pyridine-3,5-dicarboxylate

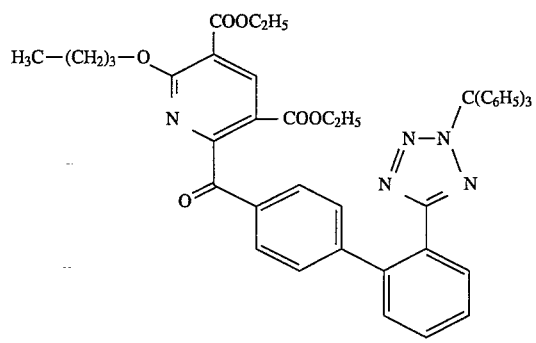

A suspension of 70.9 mg (0.15 mmol) of the compound from Example IV, 79.3 mg (0.18 mmol) of 3-(2'-triphenylmethyl-2'H-tetrazol-5'-yl)phenylboronic acid, 20 mg (0.18 mmol) of sodium carbonate, 10 mg (0.008 mmol) of tetrakis(triphenylphosphine)palladium, 0.5 ml of water, 0.5 ml of methanol and 3 ml of toluene is stirred at 90° C. under argon for 4 hours. The reaction mixture is partitioned between water and ethyl acetate, the aqueous phase is washed three times with ethyl acetate and the combined organic phases are washed with water and sodium chloride solution and dried over sodium sulphate. After the solvent has been removed, the resulting oil is chromatographed over 70 g of silica gel using ethyl acetate/petroleum ether (1: 5) to give 36.9 mg of the title compound.

Yield: 30.2% of theory MS (SIMS): 892 (M+Ag), 808 (M+Na)

EXAMPLE 2

Diethyl 1-butyl-2-oxo-6-[2'-(2-triphenylmethyl-tetrazolyl-5-yl)-biphenyl-4-ylmethyl]-1,2-dihydropyridine-3,5-dicarboxylate

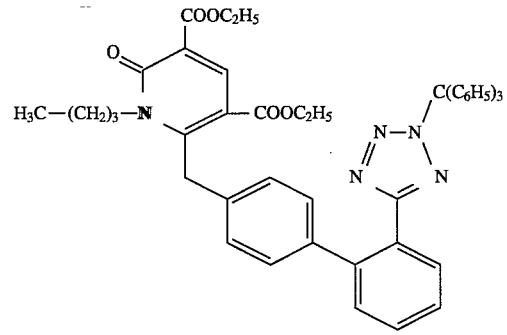

The title compound is obtained analogously to Example 1 starting from the compound of Example IX.

$R_f$ (silica gel, ethyl acetate/petroleumether 1:2)=0.38

EXAMPLE 3

Diethyl 6-butoxy-2-[2'-(1H-tetrazol-5-yl)-biphenyl-4-carbonyl]pyridine-3,5-dicarboxylate

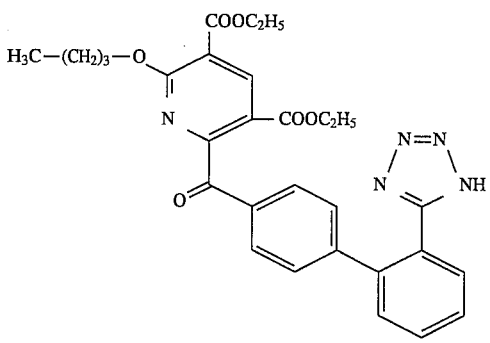

One drop of concentrated hydrochloric acid is added to a solution of 30 mg (0.04 mmol) of the compound from Example 1 in 2 ml of methanol and the mixture is stirred at 20° C. for 3 hours. The reaction mixture is diluted with water and washed three times with ethyl acetate, the combined organic phases are washed with water and sodium chloride solution, dried over sodium sulphate and concentrated and the residue is chromatographed over 25 g of silica gel using methylene chloride/methanol 10:1 to give 15.9 mg of the title compound.

Yield: 84.6% of theory MS: 544 (M+1)

EXAMPLE 4

5-Butyl 3-ethyl 6-butoxy-2-[2'-(1H-tetrazol-5-yl)-biphenyl-4-carbonyl]-pyridine-3,5-dicarboxylate

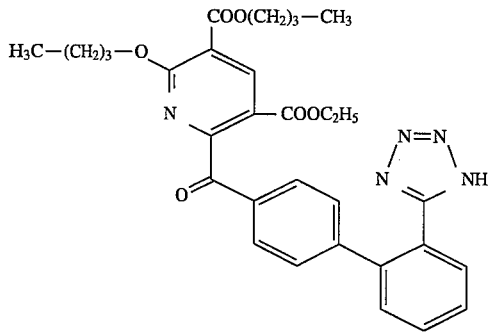

The title compound is obtained analogously to Example 1 and Example 3 from the compound of Example V.
MS (FAB): 572 (M+1)

EXAMPLE 5

Potassium salt of 5-butyl 3-ethyl 6-butoxy-2-[2'-(1H-tetrazol-5-yl)-biphenyl-4-carbonyl]-pyridine-3,5-dicarboxylate

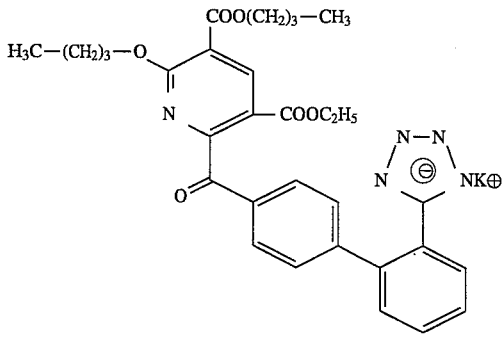

A solution of 4.1 mg (0.041 mmol) of potassium bicarbonate in 1 ml of water is added to a solution of 22.7 mg (0.041 mmol) of the compound from Example 4 in 1.5 ml of methanol/1.5 ml of tetrahydrofuran. The mixture is concentrated and the aqueous solution is lyophilized.

Yield: 25 mg, 100% of theory MS (FAB): 610 (M$^+$), 648 (M-1+K)

EXAMPLE 6

Diethyl 6-butoxy-2-{1-[2'-(1H-tetrazol-5-yl)-biphenyl-4-yl]-pentyl}-pyridine-3,5-dicarboxylate

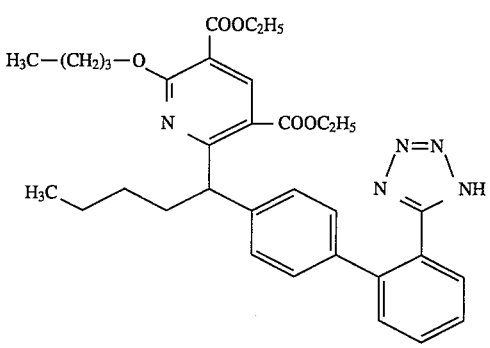

The title compound is obtained analogously to Example 1 and Example 3 from the compound of Example VI.

$R_f$ (silica gel, methylene chloride/methanol 20:1)=0.33

EXAMPLE 7

Diethyl 1-butyl-2-oxo-6-[2'-(1H-tetrazol-5-yl)-biphenyl-4-ylmethyl]-1,2-dihydropyridine-3,5-dicarboxylate

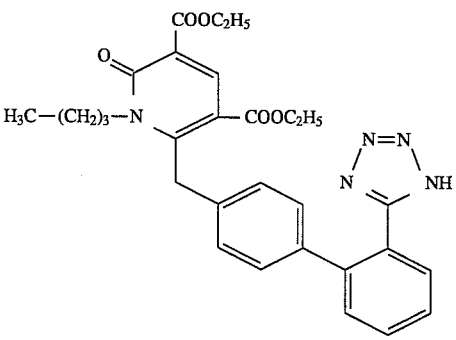

The title compound is obtained analogously to Example 3 starting from the compound of Example 2.
MS (FAB): 530, 531

EXAMPLE 8

Potassium salt of diethyl 1-butyl-2-oxo-6-[2'-(1H-tetrazol-5-yl)-biphenyl-4-ylmethyl]-1,2-dihydropyridine-3,5-dicarboxylate

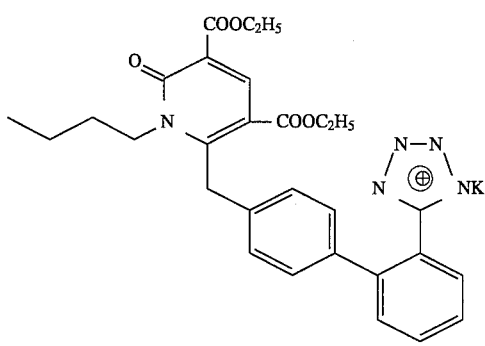

The title compound is obtained analogously to Example 5 from the compound of Example 7.

MS (FAB): 530 (M+1), 568 (M+K), 606 (M-1+2 K), 646 (M+K)

EXAMPLE 9

1-Butyl-2-oxo-6-[2'-(1H-tetrazol-5-yl)-biphenyl-4-yl-methyl]-1,2-dihydropyridine-3,5-dicarboxylic acid

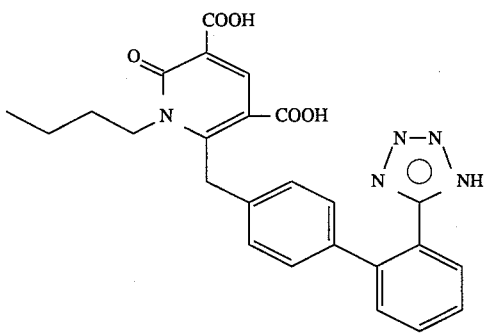

A solution of 100 mg (0.19 mmol) of the compound from Example 7 in ethanol is stirred with 200 ml (3.5 mmol) of potassium hydroxide at 20° C. overnight. The mixture is concentrated to half and concentrated hydrochloric acid is added, a colourless solid precipitating. After the solid has been filtered off with suction and dried under a high vacuum, 80 mg of the title compound are obtained.

EXAMPLE 10

Dipotassium salt of 1-butyl-2-oxo-6-[2'-(1H-tetrazol-5-yl)-biphenyl-4-ylmethyl]-1,2-dihydropyridine-3,5-dicarboxylic acid

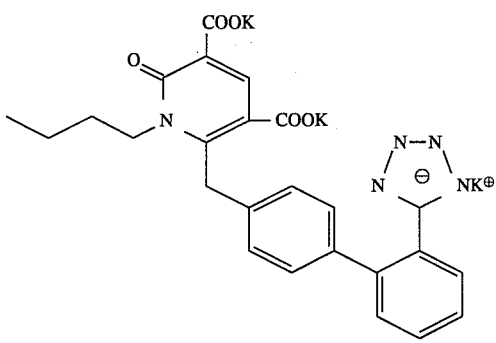

A solution of 50 mg (0.1 mmol) of the compound from Example 9 and 3.18 ml (0.32 mmol) of a 0.1N potassium hydroxide solution in water is freeze dried and the product is dried over phosphorus pentoxide under a high vaccum.

Yield: 63 mg (100% of theory) MS (FAB): 474 (M+1), 512 (M+K), 550 (M+2 K–H), 588 (M+K)

EXAMPLE 11

3-Ethyl 5-methyl 1-butyl-2-oxo-6-[2'-(2-triphenylmethyl-tetrazol-5-yl)-biphenyl-4-ylmethyl]-1,2-dihydropyridine-3,5-dicarboxylate

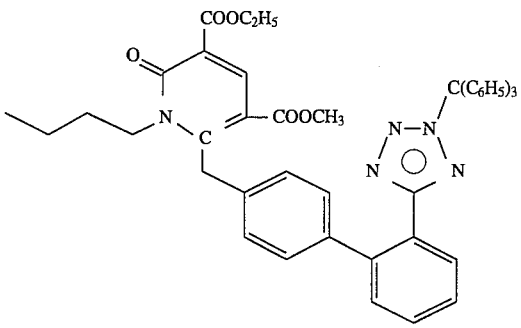

The title compound is obtained analogously to Example 1 starting from the compound of Example XII Yield: 21.5% $R_f$ (petroleum ether/ethyl acetate 2:1, silica gel)=0.37

EXAMPLE 12

3-Ethyl 5-methyl 1-butyl-2-oxo-6-[2'-(1H-tetrazol-5-yl)biphenyl-4-ylmethyl]-1,2-dihydropyridine-3,5-dicarboxylate

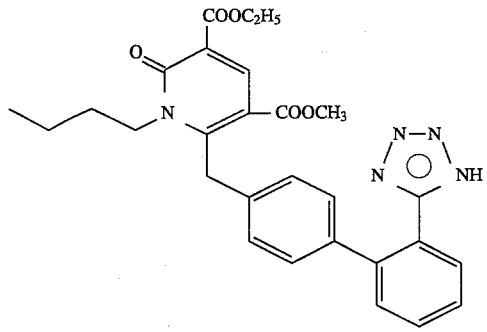

The title compound is obtained analogously to Example 3 starting from the compound of Example 11.

Yield: 43% of theory MS (FAB): 516 (M+1)

We claim:

1. A substituted pyridine or 2-oxo-1,2-dihydropyridine of the formula

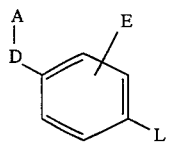

(I)

in which

A represents a radical of the formula

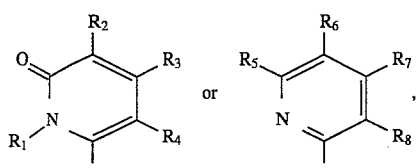

wherein
R$^1$ denotes alkyl having up to 10 carbon atoms, which is optionally substituted by cycloalkyl having 3 to 6 carbon atoms, hydroxyl or by alkoxy or alkylthio having in each case up to 6 carbon atoms, or denotes cycloalkyl having 3 to 6 carbon atoms, R$^2$, R$^5$ and R$^6$ are identical or different and denote hydrogen, hydroxyl, nitro, cyano, formyl or halogen, or denote alkyl, alkenyl, alkinyl, alkoxy or alkylthio having in each case up to 8 carbon atoms, which are optionally substituted up to 3 times in an identical or different manner by hydroxyl, cyano, halogen, carboxyl, alkoxy, acyl or alkoxycarbonyl having in each case up to 6 carbon atoms, or by cycloalkyl having 3 to 6 carbon atoms, benzyl, phenyl, phenoxy, or benzoyl wherein said cyclic radicals are optionally substituted up to 2 times in an identical or different manner by trifluoromethyl, trifluoromethoxy, halogen, nitro, cyano, hydroxyl, hydroxymethyl or by alkyl or alkoxy having in each case up to 6 carbon atoms, or denote acyl or alkoxycarbonyl having in each case up to 8 carbon atoms, phenoxycarbonyl, benzyloxycarbonyl or carboxyl, or denote tetrazolyl, which is optionally substituted by triphenylmethyl or by alkyl having up to 6 carbon atoms, which can in turn be substituted by cyano, halogen, carboxyl, phenoxycarbonyl, hydroxyl or by straight-chain or branched alkoxy or alkoxycarbonyl having in each case up to 6 carbon atoms, or denote a group of the formula

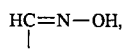

—NR$^9$R$^{10}$, —CO—NR$^{11}$R$^{12}$, —CH$_2$—OR$^{13}$ or —S(O)$_a$—R$^{14}$ wherein
R$^9$, R$^{10}$, R$^{11}$ and R$^{12}$ are identical or different and denote hydrogen, cycloalkyl having 3 to 8 carbon atoms or alkyl having up to 8 carbon atoms, which is optionally substituted by phenyl, R$^{13}$ denotes acyl having up to 6 carbon atoms or benzoyl, R$^{14}$ denotes alkyl having up to 8 carbon atoms, a denotes a number 1 or 2, R$^3$ and R$^7$ are identical or different and denote hydrogen, hydroxyl, carboxyl, alkoxy or alkoxycarbonyl having in each case up to 8 carbon atoms, or denote a group of the formula —NR$^{15}$R$^{16}$, wherein
R$^{15}$ and R$^{16}$ have the abovementioned meaning of R$^9$ and R$^{10}$ and are identical to or different from these, or
denote aryl having 6 to 10 carbon atoms, which is optionally substituted up to 2 times in an identical or different manner by trifluoromethyl, trifluoromethoxy, halogen, nitro, cyano, hydroxyl, hydroxymethyl or by straight-chain or branched alkyl or alkoxy having in each case up to 6 carbon atoms, or denote straight-chain or branched alkyl or alkenyl having in each case up to 8 carbon atoms, which is optionally substituted up to 3 times in an identical or different manner by hydroxyl, cyano, halogen, carboxyl, straight-chain or branched alkoxy, acyl or alkoxycarbonyl having in each case up to 6 carbon atoms, or by cycloalkyl having 3 to 6 carbon atoms, benzyl, phenyl, phenoxy, or benzoyl wherein said cyclic radicals are optionally substituted up to 2 times in an identical or different manner by trifluoromethyl, trifluoromethoxy, halogen, nitro, cyano, hydroxyl, hydroxymethyl or by alkyl or alkoxy having in each case up to 6 carbon atoms, R$^4$ denotes hydrogen, nitro, carboxyl or alkoxycarbonyl having up to 8 carbon atoms, or denotes a group of the formula —NR$^{17}$R$^{18}$, wherein
R$^{17}$ and R$^{18}$ have the abovementioned meaning of R$^9$ and R$^{10}$ and are identical to or different from these, or
denotes alkyl or alkenyl having in each case up to 8 carbon atoms, which is optionally substituted up to 3 times in an identical or different manner by hydroxyl, cyano, halogen, carboxyl, straight-chain or branched alkoxy, acyl or alkoxycarbonyl having in each case up to 6 carbon atoms, or by cycloalkyl having 3 to 6 carbon atoms, benzyl, phenyl, or benzoyl, wherein said cyclic radicals are optionally substituted up to 2 times in an identical or different manner by trifluoromethyl, trifluoromethoxy, halogen, nitro, cyano, hydroxyl, hydroxymethyl or by alkyl or alkoxy having in each case up to 6 carbon atoms, R$^8$ has the abovementioned meaning of R$^1$ and R$^4$ and is identical to or different from these, D represents the

group or
represents a group of the formula

wherein
T denotes hydrogen or alkyl having up to 8 carbon atoms,

E represents hydrogen, halogen, cyano, nitro, trifluoromethyl, hydroxyl, trifluoromethoxy or amido, or represents alkyl, alkoxy or alkoxycarbonyl having in each case up to 6 carbon atoms, L represents a radical of the formula

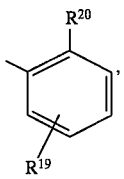

wherein
R$^{19}$ has the abovementioned meaning of E and is identical to or different from this, and
R$^{20}$ denotes a radical of the formula

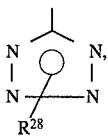

wherein $R^{28}$ denotes hydrogen or straight-chain or branched alkyl having up to 8 carbon atoms, which is optionally substituted by acyl having up to 6 carbon atoms, or denotes the triphenylmethyl group, or a salt thereof, the compound having at most three tetrazole groups.

2. A substituted pyridine or 2-oxo-1,2-dihydropyridine according to claim 1, wherein A represents a radical of the formula

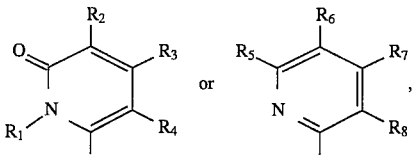

wherein $R^1$ denotes hydrogen or alkyl having in each case up to 8 carbon atoms, which is optionally substituted by cyclopropyl, cyclopentyl, cyclohexyl, hydroxyl or by alkoxy or alkylthio having in each case up to 4 carbon atoms, or denotes cyclopropyl, cyclopentyl or cyclohexyl, $R^2$, $R^5$ and $R^6$ are identical or different and denote hydrogen, hydroxyl, nitro, cyano, formyl, fluorine, chlorine, bromine or iodine, or denote alkyl, alkenyl, alkinyl, alkoxy or alkylthio having in each case up to 6 carbon atoms, which are optionally substituted by hydroxyl, cyano, fluorine, chlorine, bromine, carboxyl, alkoxy, acyl or alkoxycarbonyl having in each case up to 4 carbon atoms, or by benzoyl, phenyl, or benzoyl wherein said cyclic radicals are optionally substituted by trifluoromethoxy, trifluoromethyl, hydroxymethyl, fluorine, chlorine, bromine, iodine or by alkyl or alkoxy having in each case up to 6 carbon atoms, or denote acyl or alkoxycarbonyl having in each case up to 6 carbon atoms, phenoxycarbonyl, benzyloxycarbonyl or carboxyl, or 'denote tetrazolyl, which is optionally substituted by triphenylmethyl or by alkyl having up to 5 carbon atoms, which can in turn be substituted by cyano, fluorine, chlorine, bromine, carboxyl, hydroxyl or by alkoxy or alkoxycarbonyl having in each case up to 4 carbon atoms, or denote a group of the formula

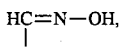

$-NR^9R^{10}$, $-CO-NR^{11}R^{12}$, $-CH_2-OR^{13}$ or $-S(O)_a-R^{14}$ wherein $R^9$, $R^{10}$, $R^{11}$ and $R^{12}$ are identical or different and denote hydrogen, cyclopropyl, cyclopentyl, cyclohexyl or alkyl having up to 6 carbon atoms, which is optionally substituted by phenyl, $R^{13}$ denotes acyl having up to 6 carbon atoms or benzoyl, $R^{14}$ denotes alkyl having up to 6 carbon atoms, a denotes a number 1 or 2, $R^3$ and $R^7$ are identical or different and denote hydrogen, hydroxyl, carboxyl or alkoxy or alkoxycarbonyl having in each case up to 6 carbon atoms, or denote a group of the formula $-NR^{15}R^{16}$, wherein $R^{15}$ and $R^{16}$ have the abovementioned meaning of $R^9$ and $R^{10}$ and are identical to or different from these, or denote phenyl, which can optionally be substituted by trifluoromethoxy, triflouromethyl, hydroxymethyl, fluorine, chlorine, bromine, iodine or by alkyl or alkoxy having in each case up to 6 carbon atoms, or denote alkyl or alkenyl having in each case up to 6 carbon atoms, which are optionally substituted by hydroxyl, cyano, fluorine, chlorine, bromine, carboxyl, alkoxy, acyl or alkoxycarbonyl having in each case up to 4 carbon atoms, or by benzyl, phenyl, phenoxy, benzoyl, wherein the cyclic radicals are optionally substituted by trifluoromethyl, hydroxymethyl, fluorine, chlorine, bromine, iodine, or by alkyl or alkoxy having in each case up to 6 carbon atoms, $R^4$ denotes hydrogen, nitro, carboxyl or alkoxycarbonyl having up to 6 carbon atoms, or denotes a group of the formula $-NR^{17}R^{18}$, wherein $R^{17}$ and $R^{18}$ have the abovementioned meaning of $R^9$ and $R^{10}$ and are identical to or different from these, or denotes alkyl or alkenyl having in each case up to 6 carbon atoms, which are optionally substituted by hydroxyl, cyano, fluorine, chlorine, bromine, carboxyl, alkoxy, acyl or alkoxycarbonyl having in each case up to 4 carbon atoms, or by benzyl, phenyl, phenoxy, benzoyl or thienyl, it being possible for the cyclic radicals in turn to be substituted by trifluoromethoxy, trifluoromethyl, hydroxymethyl, fluorine, chlorine, bromine, iodine or by alkyl or alkoxy having in each case up to 6 carbon atoms, $R^8$ has the abovementioned meaning of $R^1$ and $R^4$ and is identical to or different from these, D represents the

group or represents a group of the formula

wherein

T denotes hydrogen or alkyl having up to 7 carbon atoms,

E represents hydrogen, fluorine, chlorine, bromine, cyano, nitro, methoxy, amido, trifluoromethyl or trifluoromethoxy, or represents alkyl or alkoxycarbonyl having in each case up to 4 carbon atoms, L represents a radical of the formula

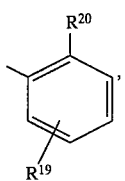

wherein $R^{19}$ has the abovementioned meaning of D and is identical to or different from this and $R^{20}$ denotes a radical of the formula

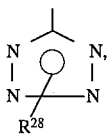

wherein $R^{28}$ denotes hydrogen or alkyl having up to 6 carbon atoms, which is optionally substituted by acyl having up to 4 carbon atoms, or denotes the triphenylmethyl group, or a salt thereof.

3. A substituted pyridine or 2-oxo-1,2-dihydropyridine according to claim 1, wherein represents a radical of the formula

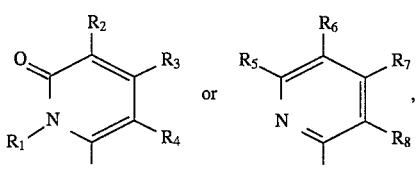

wherein $R^1$ denotes hydrogen or alkyl having up to 6 carbon atoms, which is optionally substituted by hydroxyl or alkoxy having in each case up to 3 carbon atoms, or denotes cyclopropyl, cyclopentyl or cyclohexyl, $R^2$ and $R^6$ are identical or different and denote hydrogen, cyano, formyl, fluorine, chlorine, bromine or iodine, or represent alkyl or alkoxy having in each case up to 4 carbon atoms, or denote alkoxycarbonyl having in each case up to 4 carbon atoms, phenoxycarbonyl, benzyloxycarbonyl or carboxyl, or denote tetrazolyl, which is optionally substituted by triphenylmethyl or by alkyl having up to 4 carbon atoms, or denote $-NR^9R^{10}$, $-CO-NR^{11}R^{12}$ or $-CH_2-OR^{13}$ wherein $R^9$, $R^{10}$, $R^{11}$ and $R^{12}$ are identical or different and denote hydrogen, cyclopropyl, cyclopentyl or alkyl having up to 4 carbon atoms, which is optionally substituted by phenyl, $R^{13}$ denotes acyl having up to 4 carbon atoms or benzoyl, $R^5$ denotes hydroxyl or alkyl or alkoxy having in each case up to 6 carbon atoms, $R^3$ and $R^7$ are identical or different and denote hydrogen, hydroxyl, carboxyl, alkoxy or alkoxycarbonyl having in each case up to 4 carbon atoms, or denote a group of the formula $-NR^{15}R^{16}$, wherein $R^{15}$ and $R^{16}$ have the abovementioned meaning of $R^9$ and $R^{10}$ and are identical to or different from these, or denote phenyl, vinyl or alkyl having up to 5 carbon atoms, $R^4$ denotes hydrogen, carboxyl or alkoxycarbonyl having up to 4 carbon atoms, or denotes a group of the formula $-NR^{17}R^{18}$, wherein $R^{17}$ and $R^{18}$ have the abovementioned meaning of $R^9$ and $R^{10}$ and are identical to or different from these, or denotes vinyl or alkyl having up to 4 carbon atoms, $R^8$ has the abovementioned meaning of $R^1$ and $R^4$ and is identical to or different from these, D represents the

group or represents a group of the formula

wherein

T denotes hydrogen or alkyl having up to 5 carbon atoms,

E represents hydrogen, fluorine, chlorine, bromine, cyano, methoxy, trifluoromethyl or alkyl or alkoxycarbonyl having in each case up to 3 carbon atoms and L represents a radical of the formula

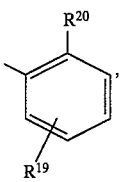

wherein $R^{19}$ denotes hydrogen, and $R^{20}$ denotes the tetrazolyl radical of the formula

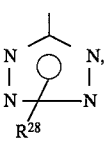

wherein $R^{28}$ denotes hydrogen or alkyl having up to 4 carbon atoms, or denotes the triphenylmethyl group, or a salt thereof.

4. A substituted pyridine or 2-oxo-1,2-dihydropyridine according to claim 1, wherein A represents a radical of the formula

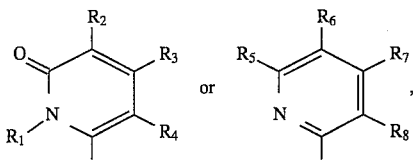

or wherein $R^1$ denotes alkyl having up to 4 carbon atoms, $R^2$ and $R^6$ are identical or different and denote hydrogen, carboxyl or alkoxycarbonyl having up to 4 carbon atoms, $R^5$ denotes hydroxyl or alkyl or alkoxy having up to 4 carbon atoms, $R^3$ and $R^7$ are identical or different and denote hydrogen, hydroxyl, carboxyl or alkoxy or alkoxycarbonyl having in each case up to 4 carbon atoms, $R^4$ denotes hydrogen, carboxyl or alkoxycarbonyl having up to 4 carbon atoms, $R^8$ has the abovementioned meaning of $R^1$ and $R^4$ and is identical to or different from these, D represents the >C=O group or represents a group of the formula >CH—T, wherein T denotes hydrogen or alkyl having up to 4 carbon atoms, E represents hydrogen, fluorine, chlorine, trifluoromethyl or cyano, and L represents a radical of the formula

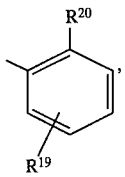

wherein $R^{19}$ denotes hydrogen, and $R^{20}$ denotes the tetrazolyl radical of the formula

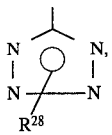

wherein $R^{28}$ denotes hydrogen or the triphenylmethyl group, or a salt thereof.

5. A substituted pyridine according to claim 1 wherein such compound is diethyl 6-butoxy-2-[2'-(1H-tetrazol-5-yl)-biphenyl-4-carbonyl]pyridine-3,5-dicarboxylate and has the formula

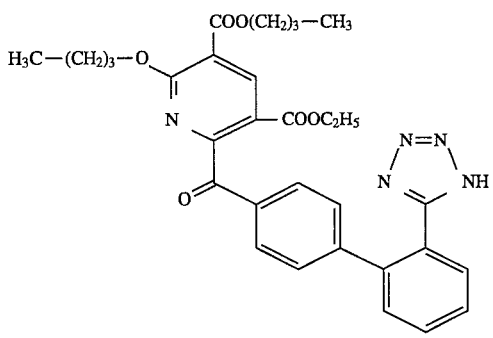

or a salt thereof.

6. A substituted 2-oxo-1,2-dihyropyridine according to claim 1 wherein such compound is 5-Butyl 3-ethyl 6-butoxy-2-[2'-(1H-tetrazo-5-yl)-biphenyl-4-carbonyl]-pyridine-3,5-dicarboxylate and has the formula

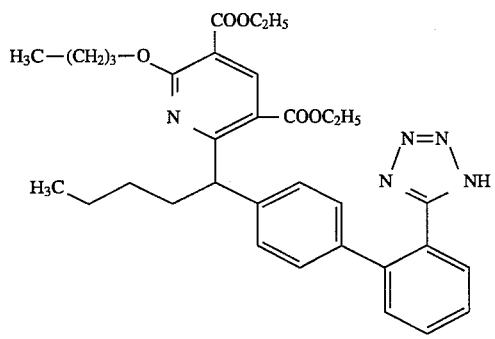

or a salt thereof.

7. A substituted pyridine according to claim 1 wherein such compound is diethyl 6-butoxy-2-}1-[2'-(1H-tetrazol-5-yl)-biphenyl-4-yl]-pentyl}-pyridine-3,5-dicarboxylate which has the formula or a salt thereof.

8. A substituted 2-oxy 1,2-dihydropyridine according to claim 1 wherein such compound is diethyl 1-butyl-2-oxo-6-[2'-(1H-tetrazol-5-yl)-biphenyl-4-yl-methyl]-1,2-dihydropyridine-3,5-dicarboxylate which has the formula

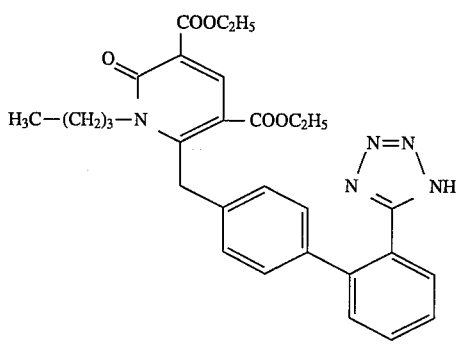

or a salt thereof.

9. A substituted 2-oxo-1,2-dihydropyridine according to claim 1 wherein such compound is 1-Butyl-2-oxo-6-[2'-(1H-tetrazol-5-yl)-biphenyl-4-yl-methyl]-1,2-dihyropyridine-3,5-dicarboxylic acid which has the formula

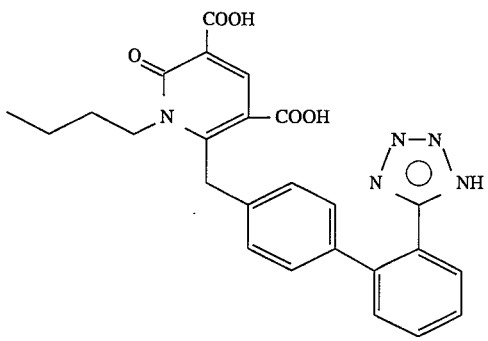

or a salt thereof.

10. A composition for the treatment of arterial hypertension and atherosclerosis comprising an amount effective thereof of a compound or salt thereof according to claim 1 and a pharmacologically acceptable diluent.

* * * * *